United States Patent [19]

Sung

[11] 4,294,585

[45] Oct. 13, 1981

[54] NOVEL FUEL COMPOSITION FOR INTERNAL COMBUSTION ENGINE

[75] Inventor: Rodney L. Sung, Fishkill, N.Y.

[73] Assignee: Texaco Inc., White Plains, N.Y.

[21] Appl. No.: 189,530

[22] Filed: Sep. 22, 1980

[51] Int. Cl.$^3$ ............................. C10L 1/18; C10L 1/22
[52] U.S. Cl. ............................................. 44/53; 44/56; 44/63; 548/251; 252/390; 252/394
[58] Field of Search ............... 44/53, 56, 63; 252/390, 252/394; 548/251

[56] References Cited

U.S. PATENT DOCUMENTS

| | | | |
|---|---|---|---|
| 3,316,176 | 4/1967 | Michalski et al. | 252/390 |
| 3,752,764 | 8/1973 | Sullivan | 252/390 |

*Primary Examiner*—Jacqueline V. Howard
*Attorney, Agent, or Firm*—Carl G. Ries; Robert A. Kulason; Carl G. Seutter

[57] ABSTRACT

A novel fuel composition contains ethanol or gasohol plus, as a corrosion inhibitor, a reaction product of aminotetrazole, formaldehyde, and an N-alkyl propylene diamine.

46 Claims, No Drawings

NOVEL FUEL COMPOSITION FOR INTERNAL COMBUSTION ENGINE

FIELD OF THE INVENTION

This invention relates to a fuel composition for internal combustion engines particularly characterized by corrosion inhibition.

BACKGROUND OF THE INVENTION

As is well known to those skilled in the art, fuel compositions typified by gasohol and alcohols which are to be considered for commercial use must possess low corrosion activity; and this may be effected by addition thereto of various corrosion inhibition systems. It is an object of this invention to provide a fuel composition for internal combustion engines particularly characterized by corrosion inhibition. Other objects will be apparent to those skilled in the art.

STATEMENT OF THE INVENTION

In accordance with certain of its aspects, the fuel composition of this invention may comprise (a) a major portion of a fuel containing (i) at least one alcohol selected from the group consisting of ethanol and methanol and (ii) gasoline in amount of 0–50 volumes per volume of alcohol; and (b) a minor corrosion inhibiting amount of, as a corrosion inhibiting agent, a reaction product of (i) an aminotetrazole, (ii) an aldehyde or a ketone, and (iii) a $C_3$–$C_{12}$ poly-primary amine bearing at least one —NHR' group wherein R' is a $C_{12}$–$C_{18}$ hydrocarbon group.

DESCRIPTION OF THE INVENTION

The fuel for internal combustion engines which may be treated by the process of this invention may contain (i) at least one alcohol selected from the group consisting of ethanol and methanol and (ii) gasoline in amount of 0–50 volumes per volume of alcohol. The fuel may be an alcohol-type fuel containing little or no hydrocarbon. Typical of such fuels are methanol, ethanol, mixtures of methanol-ethanol, etc. Commercially available mixtures may be employed. Illustrative of one such commercially available mixture may be that having the following typical analysis.

TABLE I

| Component | Parts |
|---|---|
| ethanol | 3157.2 |
| methyl isobutyl ketone | 126.3 |
| acetic acid | 0.256 |
| methyl alcohol | 0.24 |
| isopropyl alcohol | 0.2 |
| n-propyl alcohol | 0.162 |
| ethyl acetate | 0.2 |

The fuels which may be treated by the process of this invention include gasohols which may be formed by mixing 90–95 volumes of gasoline with 5–10 volumes of ethanol or methanol. A typical gasohol may contain 90 volumes of gasoline and 10 volumes of absolute alcohol.

It is preferred that the fuels to be treated by the process of this invention be substantially anhydrous i.e. that they contain less than about 0.3 v % water; typically they may contain 0.0001 v %–0.005 v %, say about 0.04 v % water.

It is a feature of these fuels that they may undesirably contain acidic contaminants which may cause serious corrosion problems. These contaminants are particularly in evidence when the alcohol is a commercially available alcohol which contains therein inter alia acids concurrently produced as by fermentation processes for producing ethanol or acids which have been picked up during handling. Acetic acid is a common acid present in the commercially available alcohols produced by fermentation; and it may be present in amount of 0.003 w %–0.005 w % of the total of the alcohol.

In accordance with practice of the process of this invention, there may be added to the fuel a minor corrosion inhibiting amount of, as a corrosion inhibiting agent, a reaction product of (i) an aminotetrazole, (ii) an aldehyde or a ketone, and (iii) a $C_3$–$C_{14}$ poly-primary amine bearing at least one free —NH$_2$ group and at least one —NHR' group wherein R' is a $C_{12}$–$C_{18}$ hydrocarbon group.

The aminotetrazoles which may be employed include 1-amino tetrazoles, 2-amino tetrazole, 3-amino tetrazoles, 4-amino tetrazoles, and 5-aminotetrazoles, including those bearing inert substituents which do not react in the instant reaction typified by hydrocarbon or alkoxy groups.

The preferred is 5-amino-1-H-tetrazole.

The aldehyde or ketone which may be employed may be one bearing aldehyde and/or ketone groups on a hydrocarbon backbone which later may be derived from alkyl, aryl, alkaryl, aralkyl, cycloalkyl hydrocarbons. Illustrative aldehydes and ketones which may be employed include:

TABLE acetaldehyde
propionaldehyde
butyraldehyde
cyclohexaldehyde
benzaldehyde
acetone
methyl ethyl ketone
acetophenone Preferred are the $C_1$–$C_8$ aldehydes; most preferred is formaldehyde which may be employed in 37% aqueous solution or as its trimer para-formaldehyde.

The amines which may be employed include polyamines, preferably diamines, which bear at least one free primary amine —NH$_2$ group and at least one substituted primary amine group. The latter may be di-substituted but more preferably it is mono-substituted. The hydrocarbon nucleus of the amine may be aliphatic or aromatic-including alkyl, alkaryl, aralkylaryl, or cycloalkyl in nature. The preferred amines may be of the formula

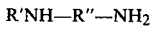

R'NH—R''—NH$_2$ i.e. monosubstituted diprimary imines. In the preferred diamines (preferably N-alkyl alkylene diamines), the R'' group may be alkylene, aralkylene, alkarylene, arylene, or cycloalkylene. The R' group may be a $C_{12}$–$C_{18}$ alkyl, alkaryl, aralkyl, aryl, or cycloalkyl hydrocarbon moiety.

Illustrative of the preferred N-alkyl alkylene diamines may include:

A. The Duomeen O brand of N-oleoyl-1,3-propane diamine;

B. The Duomeen S brand of N-stearyl-1,3-propane diamine;

C. The Duomeen T brand of N-tallow-1,3-propane diamine.

D. The Duomeen C brand of N-coco-1,3-propane diamine.

E. The Duomeen L-11 brand of N-beta-undecyl-1,3-propane diamine.

The most preferred R'NH—R"—NH$_2$ is that wherein the R" group is propylene —CH$_2$CH$_2$CH$_2$— and the R' group may be a C$_{11}$-C$_{18}$ n-alkyl group. The preferred composition may be R'—NH—CH$_2$CH$_2$CH$_2$—NH$_2$ wherein R' is a C$_{12}$ straight chain alkyl group.

It will be apparent to those skilled in the art that the several reactants may bear inert substituents which are typified by alkyl, alkoxy, halogen, nitro, cyano, haloalkyl, etc. It will also be apparent that the preferred compounds to be employed will be those which are soluble in the solvents employed during the reaction and which produce products which are soluble in or compatible with the system in which the product is to be employed.

Typical solvents which may be employed may include alcohols as methanol, ethanol, butanols, cyclohexanol, etc. or hydrocarbons including heptane, octane, toluene, xylene, gasoline, etc. It is preferred that the solvent system include alcohol and hydrocarbon. A particularly preferred system may include equal volumes of methanol and xylene.

Formation of the desired additive may preferably be effected by placing substantially equimolar quantities of the amine and the aminotetrazole in a reaction vessel in an excess of solvent. A typical solvent (eg equal volumes of methanol and xylene) may be present in amount of 50-200 volumes, say 120 volumes per volume of the total of the other reactants. The aldehyde or ketone (in equimolar amount) may be added slowly with agitation to the reaction mixture. It is not necessary to add catalyst.

As the aldehyde or ketone is added, the following reaction occurs (in the case of 5-amino-1-H-tetrazole, formaldehyde, and N-monoalkyl propylene diamines).

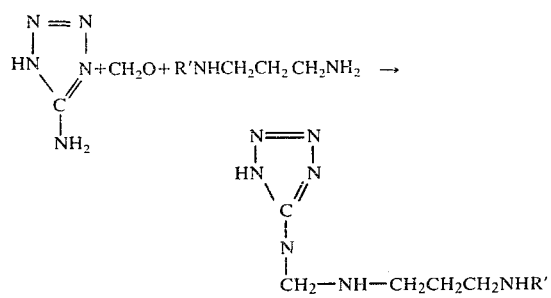

wherein R' may preferably be a C$_{12}$-C$_{18}$ alkyl such as oleoyl or tallowyl.

During and after addition of the aldehyde, the reaction mixture may be refluxed at 50° C.–80° C., say 76° C. for 5–10 hours, say 6 hours. At the end of the reaction period the reaction mixture may be cooled to ambient temperature of 20° C.–27° C., say 25° C. and filtered and then stripped (as by distillation at 80° C.–100° C., say 76° C.) of solvent.

The residue which is generally a waxy solid or viscous liquid is recovered in yield approaching stoichiometric.

The so-prepared rust and corrosion inhibitors may be added to fuels (including alcohol, gasoline, gasohol etc.) or to antifreeze. These compositions may be particularly found to be effective as rust and corrosion inhibitors when added to absolute alcohol fuels typified by those available commercially containing compounds including ethers, esters, acids, etc.

The so prepared rust and corrosion inhibitors may be added to a fuel in amount of 0.25–25 PTB, preferably 1–20 PTB, more preferably 1–10 PTB, say 10 PTB. (PTB stands for pounds of additive per thousand barrels of fuel) Alternatively expressed, the inhibitor may be added to a fuel in minor corrosion-inhibiting amount of 0.0001–0.01 w %, preferably 0.0004–0.008 w %, more preferably 0.0004–0.004 w %, say 0.004 w %. Larger amounts may be employed but may not be necessary.

It is a feature of this invention that the fuel composition so prepared is characterized by its increased corrosion and rust inhibition i.e. its decreased ability to form rust on iron surfaces in the presence of aqueous acid systems.

The corrosive nature of the formulated products may be readily measured by the Iron Strip Corrosion Test (ISCT). In this test, an iron strip (12 mm × 125 mm × 1 mm) is prepared by washing in dilute aqueous hydrochloric acid to remove mill scale, then with distilled water to remove the acid, then with acetone-followed by air drying. The strip is then polished with #100 emery cloth.

The polished strip is totally immersed in 110 ml of the test liquid in a 4 ounce bottle for 15 minutes at room temperature of 20° C. 20 ml of the test liquid is poured off and replaced with 20 ml of distilled water. The bottle is shaken as the sample is maintained for 3 hours at 90° F. The percent rust on the strip is determined visually. A second reading is taken after 40 hours.

The inhibited fuels of this invention, after 40 hours of ISCT generally show a Rust and Corrosion rating below about 2–3% and frequently as low as trace-to-1%.

DESCRIPTION OF PREFERRED EMBODIMENTS

Practice of this invention will be apparent to those skilled in the art from the following examples wherein, as elsewhere in this specification, all parts are parts by weight unless otherwise specified.

EXAMPLE I

In this example which illustrates the best mode known to me of practicing the process of this invention, there is added to 96 parts of the anhydrous alcohol composition of Table I, 4 parts of distilled water and 38.4 parts (corresponding to 10 PTB) of, as additive, the reaction product of equimolar amounts of (i) the Duomeen T brand of N-mono-tallow-1,3-propane diamine (74 parts), (ii) 5-amino-1-4-tetrazole and (iii) 37% formaldehyde (32 parts) which had been refluxed for 105 minutes in 60 parts of absolute methanol and 60 parts of xylene, the product being filtered hot and then stripped of solvent.

The resulting final composition was tested in the ISCT, and the Rust and Corrosion rating determined after 40 hours.

EXAMPLE II*

The procedure of Example I was duplicated except that the additive was 76 PTB of

EXAMPLE III

The procedure of Example I was duplicated except that no additive was present—only 4 parts of distilled water.

The results of the Iron Strip Corrosion Test were as follows:

TABLE

| Example | 40 hour Rust & Corrosion Rating |
|---|---|
| I | 0 |
| II* | 25% |
| III* | 50% |

From the above table, it will be apparent that the system of Example I, prepared in accordance with practice of the process of this invention, showed no rust and corrosion. Control Examples II–III showed 25%–50% rust and corrosion which is unsatisfactory.

Results comparable to those of Example I may be obtained when the amine reacted is:

TABLE

| Example | Amine |
|---|---|
| IV | Duomeen 0 brand of N-oleyl-1,3-propane diamine |
| V | Duomeen S brand of N-stearyl-1,3-propane diamine |
| VI | Duomeen C brand of N-cocoyl-1,3-propane-diamine |

Results comparable to those of Example I may be obtained when the aldehyde or ketone reactant is

TABLE

| Example | Reactant |
|---|---|
| VII | acetaldehyde |
| VIII | propionaldehyde |
| IX | butyraldehyde |
| X | cyclohexylaldehyde |

Results comparable to those of Example I may be obtained when the aminotetrazole reactant is:

TABLE

| Example | Aminotetrazole |
|---|---|
| XI | 1-aminotetrazole |
| XII | 2-aminotetrazole |
| XIII | 3-aminotetrazole |
| XIV | 4-aminotetrazole |

Results comparable to those of Example I may be obtained if the fuel is as follows:

TABLE

| Example | Fuel |
|---|---|
| XV | Gasohol containing 90 v % gasoline and 10 v % absolute ethanol |
| XVI | absolute ethanol |
| XVII | absolute methanol |

Although this invention has been illustrated by reference to specific embodiments, it will be apparent to those skilled in the art that various changes and modifications may be made which clearly fall within the scope of this invention.

I claim:

1. A fuel composition for internal combustion engines comprising
   (a) a major portion of a fuel containing (i) at least one alcohol selected from the group consisting of ethanol and methanol and (ii) gasoline in amount of 0–50 volumes per volume of alcohol; and
   (b) a minor corrosion inhibiting amount of, as a corrosion inhibiting agent, a reaction product of (i) an aminotetrazole, (ii) a ketone or an aldehyde, and (iii) a $C_3$–$C_{12}$ poly-primary amine bearing at least one free —$NH_2$ group and at least one —NHR' group wherein R' is a $C_{12}$–$C_{18}$ hydrocarbon group.

2. A fuel composition for internal combustion engines as claimed in claim 1 wherein said fuel is an alcohol.

3. A fuel composition for internal combustion engines as claimed in claim 1 wherein said fuel is methanol.

4. A fuel composition for internal combustion engines as claimed in claim 1 wherein said fuel is ethanol.

5. A fuel composition for internal combustion engines as claimed in claim 1 wherein said fuel is a commercial ethanol.

6. A fuel composition for internal combustion engines as claimed in claim 1 wherein said fuel is a commercial ethanol containing acid.

7. A fuel composition for internal combustion engines as claimed in claim 1 wherein said fuel is a commercial ethanol containing acetic acid.

8. A fuel composition for internal combustion engines as claimed in claim 1 wherein said fuel is a gasohol.

9. A fuel composition for internal combustion engines as claimed in claim 1 wherein said fuel is substantially anhydrous.

10. A fuel composition for internal combustion engines as claimed in claim 1 wherein said fuel contains less than 0.3 v % water.

11. A fuel composition for internal combustion engines as claimed in claim 1 wherein said aminotetrazole is 5-amino-tetrazole.

12. A fuel composition for internal combustion engines as claimed in claim 1 wherein said aminotetrazole is 1-amino-tetrazole.

13. A fuel composition for internal combustion engines as claimed in claim 1 wherein said aminotetrazole is 2-amino-tetrazole.

14. A fuel composition for internal combustion engines as claimed in claim 1 wherein said aminotetrazole is 3-amino-tetrazole.

15. A fuel composition for internal combustion engines as claimed in claim 1 wherein said aldehyde is formaldehyde.

16. A fuel composition for internal combustion engines as claimed in claim 1 wherein said aldehyde is acetaldehyde.

17. A fuel composition for internal combustion engines as claimed in claim 1 wherein said aldehyde is benzaldehyde.

18. A fuel composition for internal combustion engines as claimed in claim 1 wherein said ketone is acetone.

19. A fuel composition for internal combustion engines as claimed in claim 1 wherein said ketone is methyl ethyl ketone.

20. A fuel composition for internal combustion engines as claimed in claim 1 wherein said ketone is acetophenone.

21. A fuel composition for internal combustion engines as claimed in claim 1 wherein said amine is a diamine.

22. A fuel composition for internal combustion engines as claimed in claim 1 wherein said amine is a diamine containing an —NHR group.

23. A fuel composition for internal combustion engines as claimed in claim 1 wherein said amine is R'—NH—R"—NH$_2$, R" is alkylene, arylene, alkarylene, arylene, or cycloalkylene hydrocarbon and R is C$_{12}$-C$_{18}$ alkyl, alkaryl, aralkyl, aryl, or cycloalkyl hydrocarbon.

24. A fuel composition for internal combustion engines as claimed in claim 1 wherein said amine is R'—NH—CH$_2$CH$_2$CH$_2$NH$_2$ and R' is C$_{12}$-C$_{18}$ alkyl.

25. A fuel composition for internal combustion engines as claimed in claim 1 wherein said aminotetrazole is 5-amino-tetrazole, said aldehyde is formaldehyde, and said amine is R'NHCH$_2$CH$_2$CH$_2$NH$_2$ and R' is oleoyl or tallowyl.

26. A fuel composition for internal combustion engines as claimed in claim 1 wherein said corrosion inhibiting agent is present in minor corrosion inhibiting amount of 0.0001 w %-0.01 w % of said fuel composition.

27. A fuel composition for internal combustion engines comprising
   (a) a major portion of a fuel containing absolute ethanol, and
   (b) a minor corrosion inhibiting amount, 0.0001 w %-0.01 w % of said fuel composition, of as a corrosion inhibiting agent, a reaction product of 5-amino-tetrazole, formaldehyde, and R'NHCH$_2$CH$_2$CH$_2$NH$_2$ wherein R' is C$_{12}$-C$_{18}$ alkyl hydrocarbon.

28. A composition comprising a reaction product of (i) an aminotetrazole, (ii) a ketone or an aldehyde, and (iii) a C$_3$-C$_{12}$ poly-primary amine bearing at least one free —NH$_2$ group and at least one —NHR' group wherein R' is a C$_{12}$-C$_{18}$ hydrocarbon group.

29. A composition as claimed in claim 28 wherein said aminotetrazole is 5-amino-tetrazole.

30. A composition as claimed in claim 29 wherein said aminotetrazole is 1-amino-tetrazole.

31. A composition as claimed in claim 28 wherein said aminotetrazole is 2-amino-tetrazole.

32. A composition as claimed in claim 28 wherein said aminotetrazole is 3-amino-tetrazole.

33. A composition as claimed in claim 28 wherein said aldehyde is formaldehyde.

34. A composition as claimed in claim 28 wherein said aldehyde is acetaldehyde.

35. A composition as claimed in claim 28 wherein said aldehyde is benzaldehyde.

36. A composition as claimed in claim 28 wherein said ketone is acetone.

37. A composition as claimed in claim 28 wherein said ketone is methyl ethyl ketone.

38. A composition as claimed in claim 28 wherein said ketone is acetophenone.

39. A composition as claimed in claim 28 wherein said amine is a diamine.

40. A composition as claimed in claim 28 wherein said amine is a diamine containing an —NHR' group.

41. A composition as claimed in claim 28 wherein said amine is R'—NH—R"—NH$_2$, R" is alkylene, arylene, alkarylene, arylene, or cycloalkylene hydrocarbon and R' is C$_{12}$-C$_{18}$ alkyl, alkaryl, aralkyl, aryl, or cycloalkyl hydrocarbon.

42. A composition as claimed in claim 28 wherein said amine is R'—NH—CH$_2$CH$_2$CH$_2$NH$_2$ and R' is C$_{12}$-C$_{18}$ alkyl.

43. A composition as claimed in claim 28 wherein said aminotetrazole is 5-amino-tetrazole, said aldehyde is formaldehyde, and said amine is R'NHCH$_2$CH$_2$NH$_2$ and R' is oleoyl or tallowyl.

44. A composition as claimed in claim 28 wherein said corrosion inhibiting agent is present in minor corrosion inhibiting amount of 0.0001 w %-0.01 w % of said fuel composition.

45. A composition comprising a reaction product of 5-amino-tetrazole, formaldehyde, and R'NHCH$_2$CH$_2$CH$_2$NH$_2$ wherein R' is a C$_{12}$-C$_{18}$ alkyl hydrocarbon.

46.

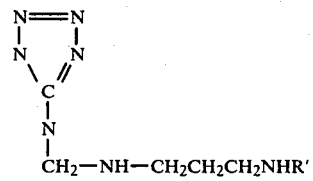

wherein R' is a C$_{12}$-C$_{18}$ straight chain alkyl hydrocarbon group.

* * * * *

UNITED STATES PATENT AND TRADEMARK OFFICE
CERTIFICATE OF CORRECTION

PATENT NO. : 4,294,585
DATED : October 13, 1981
INVENTOR(S) : Rodney L. Sung

It is certified that error appears in the above—identified patent and that said Letters Patent are hereby corrected as shown below:

| | |
|---|---|
| Col. 2, line 13 | "$C_{14}$" should read -- $C_{12}$ -- |
| Col. 2, line 56 | "imines" should read -- amines -- |
| Col. 4, bottom add | -- a commercial rust and corrosion inhibitor -- |
| Claim 22, line 68 | "R" should read -- R' --. |

Signed and Sealed this

Fifteenth Day of June 1982

[SEAL]

Attest:

Attesting Officer

GERALD J. MOSSINGHOFF

Commissioner of Patents and Trademarks